United States Patent [19]

Mizukami et al.

[11] 4,175,098

[45] Nov. 20, 1979

[54] METHOD FOR THE PREPARATION OF α-TETRALONE

[75] Inventors: Fujio Mizukami, Urawa; Juichi Imamura, Chofu, both of Japan

[73] Assignee: Director-General of the Agency of Industrial Science and Technology, Tokyo, Japan

[21] Appl. No.: 922,462

[22] Filed: Jul. 6, 1978

[30] Foreign Application Priority Data

Jul. 7, 1977 [JP] Japan .................................. 52/81153

[51] Int. Cl.² ............................................. C07C 45/02
[52] U.S. Cl. ............................... 260/590 FA; 568/734
[58] Field of Search ..................... 260/586 P, 590 FA; 568/734

[56] References Cited

U.S. PATENT DOCUMENTS

| | | | |
|---|---|---|---|
| 2,859,247 | 11/1958 | Radzitzky | 260/590 FA |
| 3,385,894 | 5/1968 | Schipper | 260/590 FA |
| 3,404,185 | 10/1968 | Thomas et al. | 260/586 P |

FOREIGN PATENT DOCUMENTS 2508334  8/1975  Fed. Rep. of Germany .... 260/590 FA

OTHER PUBLICATIONS

Feiser et al., Reagents for Organic Synthesis, p. 1110, (1975).

*Primary Examiner*—James H. Reamer
*Attorney, Agent, or Firm*—Sprung, Felfe, Horn, Lynch & Kramer

[57] ABSTRACT

A very efficient method with respect to the reaction velocity as well as the selectivity is proposed for the preparation of α-tetralone by the liquid phase oxidation of tetralin with oxygen, in which a binary catalyst is employed which is composed of a compound of chromium or cobalt soluble in the reaction mixture and an N,N-dialkyl substituted carboxylic acid amide such as N,N-dimethylformamide, N,N-dimethylacetamide and the like.

6 Claims, No Drawings

METHOD FOR THE PREPARATION OF α-TETRALONE

BACKGROUND OF THE INVENTION

The present invention relates to a novel and improved method for the preparation of α-tetralone or, in particular, to a method for the preparation of α-tetralone by the liquid phase oxidation of tetralin with oxygen in the presence of a metal catalyst.

In the conventional procedure for the synthetic preparation, α-naphthol is prepared by the sulfonation of naphthalene with sulfuric acid followed by the alkali fusion of the sulfonation product. This procedure, however, suffers from the disadvantages of the low yield of the objective α-naphthol due to the inevitable formation of the isomeric by-product β-naphthol, lower working efficiency and large volumes of noxious waste water. Therefore it is a recent trend that more and more of α-naphthol is produced by the gas-phase precious metal-catalyzed dehydrogenation of α-tetralone which is a liquid phase oxidation product of tetralin.

It is well known that the oxidation reaction of tetralin with gaseous oxygen with or without a solvent in the absence of any catalyst or in the presence of metal ions as the catalyst gives in high yields α-tetralyl hydroperoxide, α-tetralol and α-tetralone which are the selective oxidation products of tetralin oxidized at the α-position only. Two routes are proposed for the preparation of α-tetralone along the above described line of the oxidation reaction of tetralin. Firstly, highly selective oxidation of tetralin gives α-tetralyl hydroperoxide which is subsequently converted into α-tetralone by use of heavy metal ions as the catalyst (see Japanese Patent Disclosure SHO 52-10248). Secondly, α-tetralone is directly synthesized from tetralin by use of the binary catalyst composed of a soluble chromium or cobalt salt and an organic base such as amines and pyridine derivatives (see U.S. Pat. No. 3,404,183 and Japanese Patent Disclosures SHO 49-135958, 50-112347 and 51-48643).

The former method is defective because the method involves the selective synthesis of highly explosive and dangerous α-tetralyl hydroperoxide taking a long reaction time for the reaction which must be carried out at low temperatures to avoid the danger of explosion with low working efficiency. In addition, the high selectivity for the oxidative preparation of α-tetralyl hydropreoxide is obtained only when the reaction is terminated at an early stage where the conversion of tetralin is relatively low leading to increased production cost if not to mention the economical disadvantage inherent to the two-step reaction of the process.

The latter method is disadvantageous by the low selectivity for α-tetralone, especially, when a cobalt salt is used as the catalyst, with the formation of large amount of α-tetralol with relative uselessness as an industrial chemical. What is worse, the boiling point of α-tetralol is very close to that of α-tetralone. Consequently the feed material of α-tetralone in the dehydrogenation process for the preparation of α-naphthol necessarily contains considerable amount of α-tetralol as an impurity which is dehydrated into 1,2-dihydronaphthalene which is further dehydrogenated into naphthalene. Thus the preparation of α-naphthol starting with an intermediate containing large amount of α-tetralol is very disadvantageous in the process efficiency.

The latter method by use of a chromium salt as the catalyst is also disadvantageous though somewhat differently. Namely, the method is very excellent in so far as only the selectivity with respect to the relative yield of α-tetralone to α-tetralol concerns because the yield of α-tetralone is 10 to 50 times higher than the yield of α-tetralol but the method is not practical in the standpoints of economy and working efficiency due to the necessity of large amount of expensive organic bases of pyridine derivatives as well as to the very low reaction velocity and the low conversion of tetralin. Moreover, the inventors have established experimentally that large amount of α-tetralyl hydroperoxide is always formed as the by-product in the latter method in which tetralin is oxidized with gaseous oxygen in liquid phase without solvents in the presence of a pyridine base even by use of a sufficient amount of the soluble chromium salt or cobalt salt. Although the examples in the above recited Japanese Patent Disclosures are silent on the formation of the hydroperoxide, it may be a fair assumption that this method is not recommendable as an industrial procedure for the preparation of α-tetralone because of the formation of so large amount of the hydroperoxide which might be formed also in the examples of the prior art disclosures.

SUMMARY OF THE INVENTION

The object of the present invention is therefore to provide a novel and improved method for the preparation of α-tetralone free from the above described problems in the prior art methods, in which tetralin is oxidized with gaseous oxygen or oxygen-containing gas in liquid phase at a temperature of 30°–150° C. in the presence of a binary catalyst composed of at least one metal component selected from soluble chromium compounds and soluble cobalt compounds and at least one of N,N-dialkyl substituted carboxylic acid amides. The method of this invention is superior not only in the selectivity of the formation of the objective α-tetralone with respect to the relative yield of α-tetralone to α-tetralol as well as the relative yield of α-tetralone to α-tetralyl hydroperoxide but also in the productivity with high reaction velocity and working efficiency owing to the absence of any solid matter precipitated in the course of the reaction carried out at a relatively mild temperature.

DETAILED DESCRIPTION OF THE PREFERRED EMBODIMENTS

The N,N-dialkyl substituted carboxylic acid amide used as one of the components of the binary catalyst in the inventive method, which also serves as a solvent, is represented by the following general formula

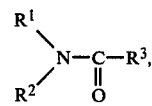

where $R^1$ and $R^2$ are each alkyl groups having 1 to 8 carbon atoms such as methyl, ethyl, propyl, butyl, octyl and cyclohexyl groups and $R^3$ is a hydrogen atom or an alkyl group having 1 to 8 carbon atoms such as methyl, ethyl, propyl, butyl and octyl groups. It is preferable that the alkyl groups $R^1$ and $R^2$ each are lower alkyl groups having 1 to 4 carbon atoms and $R^3$ is a hydrogen atom or a lower alkyl group having 1 to 4 carbon atoms in order to facilitate the separation and purification of the objective product from the reaction mixture. The use of the acid amides in which the groups $R^1$, and $R^3$ are each alkyl groups having 5 or more of carbon atoms is not recommendable because no particular advantages can be expected rather with certain difficulties in the separation of the objective product from the reaction mixture due to the proximity of their boiling points. Smaller commercial availability and expensiveness of these higher alkyl-containing acid amides should also be taken into consideration. From the standpoint of practice, the acid amide useful in the inventive method is selected from those with the combinations of the groups where $R^1$ and $R^2$ are the lower alkyl groups having 1 to 4 carbon atoms and $R^3$ is a hydrogen atom or a lower alkyl group having 1 to 4 carbon atoms. Exemplary of such acid amides are N,N-dimethylformamide, N,N-dimethylacetamide, N,N-dimethylpropionamide, N,N-diethylformamide and N,N-diethylacetamide (hereinafter abbreviated as DMF, DMA, DMP, DEF and DEA, respectively), which are satisfactory in their high activity, low expensiveness in the separation from the reaction product owing to their boiling points.

The amount of the N,N-dialkyl substituted carboxylic acid amide to be added to the reaction mixture depends largely upon whether the metal component of the catalyst is a chromium compound or a cobalt compound although influences of the kind of the acid amide, the reaction conditions and other factors cannot be neglected. When a chromium compound is used, for example, the amount of the acid amide is at least 0.06 mole or, preferably, at lest 0.27 mole per mole of tetralin although the optimum amount should be determined in accordance with the ligand or the counteranion which influences on the solubility of the chromium compound. When a cobalt compound is used, the amount of the acid amide must be increased to at least 0.87 mole or, preferably at least 150 moles per mole of tetralin although the optimum amount is also subject to variation according to the ligand or counter-anion of the cobalt compound by the similar reason to the chromium compound.

The use of the acid amide is effective in solubilizing the metal component, reducing the concentration of tetralin in the reaction mixture and accelerating the decomposition of the hydroperoxide as the by-product. As is suggested by the above recommended range in the amount of the acid amide, the optimum amount of the acid amide can be determined taking the concentration of tetralin in the reaction mixture as a measure. For example, the optimum amount of the acid amide lies within the range from 1.50 to 7.25 moles/liter or, in particular, from 1.90 to 6.50 moles/liter of the tetralin concentration when a chromium compound is used and within the range from 1.50 to 4.80 moles/liter or, in particular, from 2.00 to 3.90 moles/liter of the tetralin concentration when a cobalt compound is used. Higher concentrations of tetralin in the reaction mixture approaching a non-solvent system result in the increased formation of the hydroperoxide while smaller concentrations of tetralin result in the decreased reaction velocity, both being not recommendable by the reason of decreased productivity. No particular advantages are obtained by the use of an ordinary organic solvent other than the N,N-dialkyl substituted acid amides rather with certain problems in the separation after the reaction.

The compounds of chromium and cobalt used in the inventive method must be soluble in the reaction mixture and include salts with organic acids such as acetates, propionates, butyrates, benzoates, stearates, abietates, naphthenates and the like, inorganic salts such as nitrates, sulfates and halides, e.g. fluorides, chlorides and bromides, hydroxides and complex compounds with $\beta$-diketones such as acetylacetone, dibenzoylmethane, benzoylacetone, diethylmalonate and the like. In short, any one of the chromium and cobalt compounds can be employed in so far as it is soluble in the reaction mixture and the activity of the compounds is almost at the same level regardless of the kinds of the compounds when equimolar amounts of the compounds are added to the reaction mixture. This fact leads to a conclusion that the ions of chromium or cobalt form complexes of chromium or cobalt with the acid amide as the ligands in the reaction mixture. Therefore, certain salts of chromium and cobalt with smaller solubility as they are not mentioned above such as perchlorates and carbonates can also be used if they can be solubilized by forming complexes with the N,N-dialkyl substituted carboxylic acid amide in the reaction mixture, for example, at an elevated temperature.

The amount of the chromium compound or the cobalt compound to be added to the reaction mixture should be at least 0.0005 mole/liter, the optimum amount being of course subject to variation in accordance with the kinds of the compound and the acid amide, the reaction conditions and other factors. Lower amounts of the metal component naturally lead the reaction toward a non-catalytic reaction with very much decreased reaction velocity while larger amounts of the metal component result in the undesirable increase in the selectivity in favor of the formation of the hydroperoxide as the by-product in the sacrifice of th selectivity for the formation of the objective $\alpha$-tetralone as a consequence. Especially when the reaction is performed as a continuous process with liquid flow by use of a relatively large amount of the metal component, the excessive metal compound may deposit in some parts of the reactor leading to eventual blockage of the reactor though such a problem is not encountered when the reaction is carried out batch-wise. Thus excessive addition of the metal compound is not recommendable with no particular additional advantages. As determined with the above circumstances in consideration, the minimum concentration of the metal component is 0.0005 mole/liter and the maximum concentration of the metal component is the saturation concentration in the reaction mixture. In particular, the range of 0.0015 to 0.0300 mole/liter is recommended for a chromium and a cobalt compound. As is shown in Example 2 and Table 2 to follow, combined use of the above metal compound and an alkali metal salt such as nitrites, halides and thiocyanates is advantageous in some cases because further increase in the selectivity of $\alpha$-tetralone is obtained to some extent by the addition of small amount of the alkali metal salt.

The reaction temperature is preferably in the range from 30° to 150° C. or, more preferably, from 50° to 130° C. because lower temperatures lead naturally to the reduced reaction velocity with decreased productivity if not to mention the disadvantage caused by the necessity of obtaining large volumes of cooling water of lower temperatures to maintain the reaction temperature while higher reaction temperatures bring about the increase in the formation of the undesirable by-products in the sacrifice of the selectivity for the objective $\alpha$-tetralone.

The oxidant used in the oxidation of tetralin is an oxygen or an oxygen-containing gas which may be air or an oxygen-enriched air. When the rate of oxygen supply is sufficiently large, the reaction velocity does not depend on the oxygen partial pressure so that no pressurization is needed to increase the reaction velocity. However, it is sometimes advantageous when the reaction is carried out under an atmospheric pressure to improve the gas-liquid contact by vigorous agitation because the rate-determining step in the reaction under atmospheric pressure is the dissolution of oxygen into the reaction mixture.

It should also be noted in the inventive method that the formation of the undesirable by-products rapidly increases as the conversion of tetralin increases with consequent decrease in the selectivity for the objective α-tetralone. For example, the reaction is desirably terminated when the conversion of tetralin has reached 70% or less or 60% or less with a chromium compound or a cobalt compound as the catalyst component, respectively. On the other hand, too early termination is also disadvantageous because of the higher selectivity for the hydroperoxide in the early stage of the reaction of, say, up to 5% of the conversion of tetralin. Thus it is recommended that the reaction is scheduled to be terminated when the conversion of tetralin has reached 10 to 65% or 10 to 52% with a chromium compound or a cobalt compound as the catalyst component, respectively.

As is understood from the above description and as is shown by the examples to follow, the chromium compounds are generally preferred to the cobalt compounds with respect to the concentration range of tetralin, conversion of tetralin, selectivity for α-tetralone and the ratio of α-tetralone to α-tetralol.

The reaction of the inventive method can be performed either as a batch reaction or a continuous reaction with liquid flow. Owing to the absence of a gaseous by-product such as carbon dioxide, the supply of oxygen may be limited to only compensate the consumed amount of the oxygen or, instead, an excessive amount of oxygen may be passed through the reaction mixture. The isolation of the reaction product from the reaction mixture can be readily undertaken by distillation under a reduced pressure and accumulation of dangerous α-tetralyl hydroperoxide in the distillation residue does not take place even when small amount of the hydroperoxide is contained in the reaction mixture as such to be subjected to distillation because the hydroperoxide is decomposed mainly to α-tetralone in the course of the distillation.

Following are the examples to illustrate the method of the present invention in further detail but not to limit the scope of the invention.

EXAMPLE 1 (EXPERIMENTS NO. 1 TO NO. 11).

Into a 300 ml capacity autoclave of stainless steel equipped with a stirrer, a thermometer and a gas inlet tube were introduced 50 ml of DMF, 98.1 g of tetralin and a chromium compound as the metal component in an amount corresponding to the concentration of 0.0060 mole/liter as Cr upon dissolution and the reaction was carried out at 110±2° C. by maintaining an oxygen pressure of 20 kg/cm$^2$G while additional oxygen was continuouly introduced to compensate the consumed oxygen. When the conversion of tetralin had reached about 30% as calculated from the volume of the consumed oxygen, the introduction of oxygen was stopped and the reaction mixture was rapidly cooled as contained in the autoclave by dipping in ice-water to terminate the reaction.

The reaction mixture taken out of the autoclave was analyzed by gas chromatography for DMF, the unreacted tetralin, α-tetralone and α-tetralol and the content of α-tetralyl hydroperoxide (abbreviated hereinafter as THPO) was determined iodometrically. The reaction conditions and the results of analyses for the selectivity of α-tetralone, α-tetralol and THPO, the balance being impurities not defined, are set out in Table 1 below. The recovery of DMF was more than 96.5% in all of the experiments. In Table 1 and hereinafter, acetylacetonato-complex of chromium is abbreviated as Cr(acac)$_3$.

For comparison, the same experimental procedure was repeated excepting the use of equal molar amount of chromium (III) oxide or iron acetylacetonato-complex in place of the chromium compound. The results are also set out in Table 1. It was noted that the chromium oxide was hardly soluble in the reaction mixture.

EXAMPLE 2 (EXPERIMENTS NO. 12 TO NO. 24).

Into the same autoclave as used in Example 1 were introduced 76.8 g of tetralin, 70 ml of an acid amide and cobalt acetylacetonato-complex (abbreviated hereinafter as Co(acac)$_2$) in an amount as indicated in Table 2 below and the reaction was undertaken at 73±1° C. by maintaining the oxygen pressure of 10 kg/cm$^2$G in a similar manner to Example 1 to give the results as set out in Table 2.

The reactions in Experiments No. 13, No. 14 and No. 15 were carried out with further addition of potassium thiocyanate, sodium nitrite or lithium bromide, respectively, in an amount equal to that of Co(acac)$_2$ by moles.

Similarly, comparative experiments (Experiments No. 20 to No. 24) were undertaken under the same experimental conditions except that the acid amide was omitted or replaced with equal volume of acetic acid, acetonitrile or chlorobenzene. The results are also set out in Table 2.

EXAMPLE 3 (EXPERIMENTS NO. 25 TO NO. 35).

Into the same autoclave as used in Example 1 were introduced 122.2 g of tetralin, 25 ml of an acid amide and 0.16 g of Cr(acac)$_3$ corresponding to a concentration of 0.0030 mole/liter of Cr(acac)$_3$ with the exception of Experiment No. 26 in which equimolar amount of chromium chloride CrCl$_3$.6H$_2$O was used in place of Cr(acac)$_3$, and the reaction was carried out at a predetermined temperature in the range from 70° to 100° C. under a predetermined oxygen pressure in the range from 2.0 to 20.0 kg/cm$^2$G in a similar manner to Example 1. The results are set out in Table 3 below.

Comparative experiments (Experiments No. 33 to No. 35) were undertaken in which the acid amide was omitted or replaced with acetic acid or acetamide. In Experiments No. 33 and No. 35, chromium acetate was used instead of Cr(acac)$_3$ in a concentration of 0.0477 mole/liter or 0.0047 mole/liter, respectively. The amount of tetralin was decreased to 78.2 g in Experiment No. 33 in which the volume of acetic acid was 70 ml and pyridine was additionally added in Experiment No. 35 in an amount of 18.4 times of the chromium acetate by moles. The results of these comparative experiments are also set out in the same table.

EXAMPLE 4 (EXPERIMENTS NO. 36 TO NO. 44).

Into the same autoclave as used in Example 1 were introduced 76.8 g of tetralin, 70 ml of DMF with the exception of Experiment No. 42 in which equal volume of DMA was used instead of DMF, and a cobalt compound as indicated in Table 4 below in an amount also given in the same table and the reaction was carried out under an oxygen pressue of 30 kg/cm$^2$G at a temperature varied as shown in the table. The results are set out in Table 4.

For comparison, the concentration of Co(acac)$_2$ as the cobalt component was decreased to 0.0003 mole/liter (Experiment No. 43) or the reaction temperature was elevated above 150° C. (Experiment No. 44). The results of these comparative experiments are also set out in Table 4.

EXAMPLE 5 (EXPERIMENTS NO. 45 to NO. 65).

Into the same autoclave as used in Example 1 were introduced 150 ml of a mixture of tetralin and DMF with the exception of Experiment No. 62 in which DMA was used instead of DMF in varied proportions to give a concentration of tetralin as indicated in Table 5 below and Cr(acac)$_3$ to give a concentration as indicated in the same table with the exception of Experiment No. 61, in which chromium chloride CrCl$_3$.6H$_2$O was used instead of Cr(acac)$_3$, and the reaction was carried out under an oxygen pressure of 20 kg/cm$^2$G at a temperature as given in the table.

For comparative purpose, the reaction temperature was increased above the preferred upper limit of 150° C. (Experiments No. 63 and No. 64) or the concentration of Cr(acac)$_3$ was decreased to 0.0003 mole/liter (Experiment No. 65) and the results of these comparative experiments are also set out in the table.

EXAMPLE 6 (EXPERIMENTS NO. 66 TO NO. 71).

The same experimental procedure was repeated as in Example 5 excepting that Co(acac)$_2$ was used as the metal component instead of Cr(acac)$_3$. The results are set out in Table 6 below.

In Table 6, Experiments No. 69 to No. 71 were for comparative purpose, in which the concentration of tetralin in the reaction mixture was increased above the preferred upper limit of 4.80 moles/liter (Experiments No. 69 and No. 70) or the concentration of Co(acac)$_2$ was decreased to 0.0003 mole/liter (Experiment No. 71).

EXAMPLE 7 (EXPERIMENTS NO. 72 TO NO. 78).

Into a four-necked flask of 50 ml capacity equipped with a reflux condenser, a thermometer, a gas-tightly sealed stirrer and a gas inlet tube were taken a predetermined amount of a compound of cobalt or chromium as a metal component and a predetermined amount of an acid amide followed by flushing with nitrogen. Tetralin was introduced into the flask under a gentle stream of nitrogen in an amount to give the conentrations of the metal component and tetralin in about 150 ml of the reaction mixture as given in Table 7 below and the reaction mixture was heated to a temperature also given in the same table where the atmosphere inside the flask was replaced with oxygen and the gas inlet tube was connected to a gas holder filled with oxygen with the opening of the reflux condenser closed to make a closed reaction system. The reaction was undertaken by maintaining the oxygen pressure of the gas holder in the range from 100 to 1000 mm of water over atmospheric in accordance with the reaction temperature in order to supply oxygen to the reaction mixture under vigorous agitation to facilitate rapid absorption of oxygen into the reaction mixture. The results are shown in Table 7.

For comparison, the acid amides in the above experiments were replaced with acetic acid or acetonitrile (Experiments No. 76 and No. 77), or the chromium or cobalt compound was replaced with acetylacetonato-complex of manganese (Experiment No. 78). The results of these comparative experiments are also set out in the same table.

EXAMPLE 8 (EXPERIMENTS NO. 79 TO NO. 81)

Using the same equipment as used in Example 7, 25 ml of an acid amide or a mixture of two or three kinds of acid amides and 0.16 g of Cr(acac)$_3$ were taken into the flask followed by introduction of 125 ml of tetralin under gentle stream of nitrogen. The concentrations of Cr(acac)$_3$ and tetralin in the reaction mixture was 0.0030 mole/liter and 6.03 moles/liter, respectively. The reaction mixture was heated under vigorous agitation to reach a temperature of 90° C., where the gas inlet tube was connected to a gas holder filled with oxygen or air with the opening of the reflux condenser as opened to pass the flow of oxygen or air as blown into the reaction mixture for 5 hours at a rate of 3.6 liters/hour or 25 liters/hour, respectively, while maintaining the reaction temperature in the range from 88° to 92° C. The results are set out in Table 8 below.

Table 1

| Exp. No. | | Metal Component | Reaction time, min. | Conversion of tetralin, % | Selectivity based on reacted tetralin, % by moles | | |
|---|---|---|---|---|---|---|---|
| | | | | | α-Tetralone | α-Tetralol | THPO |
| 1 | | Cr(acac)$_3$ | 51 | 30.2 | 80.1 | 6.5 | 5.3 |
| 2 | | Cr chloride | 22 | 29.4 | 77.1 | 7.2 | 5.9 |
| 3 | | Cr nitrate | 120 | 30.4 | 81.3 | 4.9 | 4.3 |
| 4 | Present | Cr hydroxide | 105 | 29.3 | 80.4 | 4.6 | 5.3 |
| 5 | inven- | Cr sulfate | 115 | 31.3 | 76.2 | 2.7 | 9.7 |
| 6 | tion | Cr fluoride | 130 | 29.5 | 74.4 | 2.8 | 13.7 |
| 7 | | Cr naphthenate | 48 | 29.3 | 75.7 | 9.7 | 4.8 |
| 8 | | Cr acetate | 70 | 28.6 | 81.1 | 5.6 | 5.0 |
| 9 | | Cr butyrate | 75 | 29.1 | 80.2 | 5.8 | 4.9 |
| 10 | Control | Cr oxide | 320 | 29.9 | 61.5 | 2.4 | 26.9 |
| 11 | | Fe(acac)$_3$* | 60 | 38.8 | 59.9 | 6.3 | 19.1 |

*Acetylacetonato-complex of iron

Table 2

| Exp. No. | | Acid amide or Substitute | Concentration of Co (acac)$_2$, mole/liter | Reaction time, min. | Conversion of tetralin, % | Selectivity based on reacted tetralin, % by moles | | |
|---|---|---|---|---|---|---|---|---|
| | | | | | | α-Tetralone | α-Tetralol | THPO |
| 12 | | DMF | 0.0106 | 60 | 23.2 | 73.5 | 14.5 | 5.6 |
| 13 | | DMF | 0.0106 | 100 | 32.1 | 72.5 | 16.1 | 3.2 |
| 14 | Present | DMF | 0.0106 | 120 | 21.1 | 77.0 | 13.5 | 5.1 |
| 15 | inven- | DMF | 0.0106 | 60 | 22.9 | 74.4 | 15.3 | 3.8 |
| 16 | tion | DMF | 0.0079 | 70 | 28.2 | 72.8 | 14.4 | 4.3 |
| 17 | | DMF | 0.0040 | 110 | 39.4 | 72.7 | 15.1 | 3.2 |
| 18 | | DEF | 0.0026 | 180 | 41.2 | 68.4 | 9.5 | 10.3 |
| 19 | | DMA | 0.0030 | 60 | 37.3 | 71.5 | 3.4 | 10.2 |
| 20 | | Acetic acid | 0.0026 | 17 | 24.2 | 37.4 | 27.0 | 21.5 |
| 21 | | Acetic acid | 0.0477 | 7 | 20.9 | 49.1 | 32.3 | 4.8 |
| 22 | Control | Acetonitrile | 0.0477 | 15 | 21.6 | 51.2 | 37.4 | 8.1 |
| 23 | | Chlorobenzene | 0.0106 | 22 | 19.7 | 40.5 | 35.8 | 21.3 |
| 24 | | None | 0.0477 | 14 | 21.3 | 33.7 | 26.2 | 34.3 |

Table 3

| Exp. No. | | Acid amide or Substitute | Oxygen pressure, kg/cm$^2$G | Reaction temperature, °C. | Reaction time, min. | Conversion of tetralin, % | Selectivity based on reacted tetralin, % by moles | | |
|---|---|---|---|---|---|---|---|---|---|
| | | | | | | | α-Tetralone | α-Tetralol | THPO |
| 25 | | DMF | 20.0 | 71 | 450 | 18.5 | 90.7 | 2.1 | 4.7 |
| 26 | | DMF | 20.0 | 80 | 180 | 19.5 | 87.7 | 3.0 | 6.4 |
| 27 | Present | DMF | 3.0 | 90 | 240 | 27.3 | 86.2 | 3.3 | 4.6 |
| 28 | invention | DMA | 2.5 | 80 | 270 | 27.2 | 93.0 | 0.5 | 1.6 |
| 29 | | DMA | 9.5 | 80 | 260 | 41.9 | 88.3 | trace | 4.5 |
| 30 | | DMP | 6.5 | 90 | 250 | 55.8 | 83.7 | trace | 5.0 |
| 31 | | DEF | 9.5 | 90 | 180 | 34.6 | 79.4 | 4.1 | 6.0 |
| 32 | | DEA | 9.5 | 90 | 180 | 60.9 | 80.7 | trace | 5.9 |
| 33 | | Acetic acid | 20.0 | 73 | 64 | 20.3 | 30.3 | 9.4 | 50.1 |
| 34 | Control | Acetamide | 1.1 | 95 | 400 | 11.2 | 47.3 | 2.0 | 7.0 |
| 35 | | None | 20.0 | 73 | 270 | 13.0 | 18.3 | 4.4 | 74.0 |

Table 4

| Exp. No. | | Cobalt compound (mole/liter) | Reaction temperature, °C. | Reaction time, min. | Conversion of tetralin, % | Selectivity based on reacted tetralin, % by moles | | |
|---|---|---|---|---|---|---|---|---|
| | | | | | | α-Tetralone | α-Tetralol | THPO |
| 36 | | Co(acac)$_2$(0.0053) | 73 | 80 | 32.7 | 73.5 | 16.4 | 1.9 |
| 37 | Present | Nitrate (0.0050) | 92 | 60 | 41.5 | 70.2 | 11.2 | 5.9 |
| 38 | invention | Bromide (0.0050) | 91 | 120 | 51.2 | 65.1 | 7.1 | 10.8 |
| 39 | | Stearate (0.0030) | 100 | 120 | 37.2 | 67.6 | 3.4 | 10.3 |
| 40 | | Acetate (0.0050) | 96–112 | 30 | 18.7 | 70.0 | 16.1 | 2.5 |
| 41 | | Benzoate (0.0100) | 72–110 | 55 | 10.4 | 73.6 | 7.2 | 1.2 |
| 42 | | Benzoate (0.0030) | 80 | 50 | 48.6 | 71.8 | 3.3 | 12.0 |
| 43 | Control | Co(acac)$_2$(0.0003) | 75 | 270 | 53.2 | 47.1 | 3.6 | 32.4 |
| 44 | | Co(acac)$_2$(0.0213) | 151–186 | 2 | 13.1 | 53.4 | 2.9 | 20.1 |

Table 5

| Exp. No. | | Concentration of Cr (acac)$_3$, mole/liter | Concentration of tetralin, mole/liter | Reaction temperature, °C. | Reaction time, min. | Conversion of tetralin, % | Selectivity based on reacted tetralin, % by moles | | |
|---|---|---|---|---|---|---|---|---|---|
| | | | | | | | α-Tetralone | α-Tetralol | THPO |
| 45 | | 0.0266 | 3.85 | 120–128 | 30 | 34.5 | 77.1 | 9.4 | 3.0 |
| 46 | | 0.0213 | 3.85 | 90 | 200 | 27.9 | 78.6 | 8.2 | 2.7 |
| 47 | | 0.0160 | 3.85 | 103 | 100 | 31.1 | 77.3 | 8.1 | 3.6 |
| 48 | | 0.0213 | 1.94 | 90 | 180 | 14.8 | 84.3 | 10.0 | 3.2 |
| 49 | Present | 0.0267 | 2.90 | 100 | 120 | 25.1 | 82.8 | 9.2 | 1.7 |
| 50 | inven- | 0.0266 | 3.85 | 100 | 150 | 34.6 | 87.0 | 7.8 | 3.6 |
| 51 | tion | 0.0265 | 5.74 | 101 | 66 | 32.2 | 81.2 | 8.0 | 1.9 |
| 52 | | 0.0106 | 5.76 | 100 | 100 | 39.3 | 84.0 | 4.5 | 3.4 |
| 53 | | 0.0079 | 6.40 | 100 | 70 | 40.2 | 84.7 | 3.4 | 4.4 |
| 54 | | 0.0053 | 5.76 | 100 | 150 | 39.6 | 83.5 | 3.5 | 3.7 |
| 55 | | 0.0238 | 7.25 | 103 | 30 | 43.8 | 70.9 | 8.5 | 8.3 |
| 56 | | 0.0080 | 7.08 | 100 | 60 | 37.5 | 81.5 | 2.3 | 10.1 |
| 57 | | 0.0027 | 6.85 | 100 | 120 | 36.2 | 81.8 | 0.3 | 11.1 |
| 58 | | 0.0027 | 6.60 | 110 | 40 | 41.8 | 81.8 | 2.6 | 6.9 |
| 59 | | 0.0040 | 6.36 | 105 | 60 | 40.8 | 83.4 | 1.9 | 5.7 |
| 60 | | 0.0040 | 5.38 | 115 | 70 | 44.4 | 81.5 | 4.4 | 3.4 |
| 61 | | 0.0030* | 5.88 | 80 | 180 | 19.5 | 87.6 | 3.0 | 6.4 |
| 62 | | 0.0030 | 5.83 | 90 | 120 | 37.3 | 89.6 | 0.4 | 3.7 |

Table 5-continued

| Exp. No. | | Concentration of Cr (acac)₃, mole/liter | Concentration of tetralin, mole/liter | Reaction temperature, °C. | Reaction time, min. | Conversion of tetralin, % | Selectivity based on reacted tetralin, % by moles | | |
|---|---|---|---|---|---|---|---|---|---|
| | | | | | | | α-Tetralone | α-Tetralol | THPO |
| 63 | | 0.0266 | 3.85 | 155–190 | 3 | 33.6 | 54.6 | 16.1 | 3.0 |
| 64 | Control | 0.0010 | 7.25 | 153–192 | 5 | 55.3 | 48.5 | 12.7 | 4.3 |
| 65 | | 0.0003* | 7.25 | 100 | 110 | 38.3 | 56.8 | 2.4 | 31.3 |

*CrCl₃.6H₂O was used instead of Cr(acac)₃.

Table 6

| Exp. No. | | Concentration of Co(acac)₂, mole/liter | Concentration of tetralin, mole/liter | Reaction temperature, °C. | Reaction time, min. | Conversion of tetralin, % | Selectivity based on reacted tetralin, % by moles | | |
|---|---|---|---|---|---|---|---|---|---|
| | | | | | | | α-Tetralone | α-Tetralol | THPO |
| 66 | Present | 0.0212 | 3.84 | 73 | 60 | 19.8 | 73.0 | 12.2 | 8.3 |
| 67 | inven- | 0.0106 | 3.85 | 88–95 | 25 | 18.8 | 71.5 | 14.9 | 4.9 |
| 68 | tion | 0.0107 | 1.95 | 74–84 | 120 | 5.0 | 69.4 | 6.9 | 4.2 |
| 69 | | 0.0053 | 6.12 | 70 | 130 | 51.5 | 47.5 | 3.8 | 34.3 |
| 70 | Control | 0.0030 | 5.88 | 62 | 135 | 50.6 | 46.6 | 2.2 | 37.0 |
| 71 | | 0.0003 | 3.85 | 75 | 270 | 53.2 | 47.1 | 3.6 | 32.4 |

Table 7

| Exp. No. | | Metal component (mole/liter) | Acid amide or substitute | Concentration of tetralin, mole/liter | Reaction temperature, °C. | Reaction time, min. | Conversion of tetralin, % | Selectivity based on reacted tetralin, % by moles | | |
|---|---|---|---|---|---|---|---|---|---|---|
| | | | | | | | | α-Tetralone | α-Tetralol | THPO |
| 72 | | Co(acac)₂ (0.0167) | DMF | 3.87 | 51 | 176 | 21.6 | 69.8 | 12.3 | 10.8 |
| 73 | Present inven- | Co(acac)₂ (0.0112) | DEF | 3.83 | 38 | 360 | 23.8 | 67.6 | 13.4 | 9.7 |
| 74 | tion | Co benzoate (0.0029) | DMA | 3.96 | 85 | 300 | 22.3 | 68.5 | 6.2 | 7.5 |
| 75 | | Cr(acac)₃ (0.0265) | DMF | 5.83 | 85 | 150 | 16.1 | 70.9 | 12.4 | 4.8 |
| 76 | | Co acetate (0.0478) | Acetic acid | 3.85 | 51 | 120 | 22.8 | 31.1 | 54.2 | 0.7 |
| 77 | Control | Co benzoate (0.0052) | Aceto-nitrile | 3.85 | 51 | 230 | 22.1 | 49.2 | 30.0 | 6.2 |
| 78 | | Mn (acac)₂* | DMA | 3.82 | 90–95 | 240 | 12.8 | 24.7 | 10.8 | 50.8 |

*Acetylacetonato-complex of manganese

Table 8

| Exp. No. | | Acid Amide (mixing ratio by volume) | Atmosphere | Conversion of tetralin, % | Selectivity based on reacted tetralin, % by moles | | |
|---|---|---|---|---|---|---|---|
| | | | | | α-Tetralone | α-Tetralol | THPO |
| 79 | Present | DMF | Oxygen | 11.8 | 78.1 | 6.6 | 5.0 |
| 80 | Inven- tion | DMF + DMA (1:1) | Air | 12.2 | 74.2 | 8.2 | 6.1 |
| 81 | | DMF + DMP + DEA (2:2:1) | Oxygen | 11.3 | 79.3 | 6.3 | 5.4 |

What is claimed is:

1. A method for the preparation of α-tetralone which comprises oxidizing tetralin with oxygen in a homogeneous liquid phase at a temperature in the range from 30° to 150° C. in the presenc of a binary catalyst dissolved therein composed of a metal component selected from the class consisting of chromium compounds and cobalt compounds soluble in the reaction mixture in a concentration in the reaction mixture of at least 0.0005 mole/liter and an N,N-dialkyl substituted carboxylic acid amide represented by the general formula

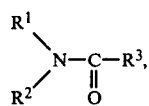

where $R^1$ and $R^2$ each are alkyl groups having 1 to 4 carbon atoms and $R^3$ is a hydrogen atom or an alkyl group having 1 to 4 carbon atoms.

2. The method as claimed in claim 1 wherein the N,N-dialkyl substituted carboxylic acid amide is selected from the class consisting of N,N-dimethylformamide, N,N-dimethylacetamide, N,N-dimethylpropionamide, N,N-diethylformamide, N,N-diethylacetamide and mixtures thereof.

3. The method as claimed in claim 1 wherein the metal component is a chromium compound and the concentration of tetralin in the reaction mixture is in the range from 1.50 to 7.25 moles/liter.

4. The method as claimed in claim 1 wherein the metal component is a cobalt compound and the concentration of tetralin in the reaction mixture is in the range from 1.50 to 4.80 moles/liter.

5. The method as claimed in claim 1 wherein the concentration of the metal component in the reaciton mixture is in the range from 0.0015 to 0.0300 mole/liter.

6. The method as claimed in claim 1 wherein the oxidation reaction of tetralin is carried out at a temperature in the range from 50° to 130° C.

* * * * *